US00PP09181P

United States Patent [19]

Dehan

[11] Patent Number: Plant 9,181

[45] Date of Patent: Jun. 27, 1995

[54] IMPATIENS PLANT NAMED 'MERENGUE'

[75] Inventor: Klara Dehan, Holon, Israel

[73] Assignee: Danziger "Dan" Flower Farm, Hashiva, Israel

[21] Appl. No.: 299,611

[22] Filed: Sep. 2, 1994

[51] Int. Cl.[6] ..... A01H 5/00

[52] U.S. Cl. ..... Plt./87.6

[58] Field of Search ..... Plt. 87.6

[56] References Cited

U.S. PATENT DOCUMENTS

P.P. 7,791 2/1992 Drewlow ..... Plt./87.6

*Primary Examiner*—James R. Feyrer

*Attorney, Agent, or Firm*—Foley & Lardner

[57] ABSTRACT

A new and distinct cultivar of Impatiens plant named Merengue, characterized by its large, light pink flowers with dark red-purple eye at base of petals; compact growth habit, excellent self-branching, dark green leaves infused with purple, pleasantly contrasting foliage and flower colors, floriferous habit, and its suitability for use both as a bedding plant and in its hanging basket culture.

1 Drawing Sheet

The present invention relates to a new and distinctive cultivar of Impatiens plant, botanically known as Impatiens, commercially known as New Guinea Impatiens, and known by the cultivar name Merengue.

The new cultivar was developed by the inventor Klara Dehan in Mishmar Hashiva, Israel in a controlled breeding program. The female or seed parent was a cultivar identified by the breeding number 6 OR, and the male or pollen parent was a cultivar identified by the breeding number 113 OR. Both parents are proprietary cultivars used in the breeding program. The new cultivar was selected by the inventor from the progeny of the stated cross.

Asexual reproduction of the new cultivar by leaf cuttings performed by the inventor in Mishmar Hashiva, Israel has established that the unique features of this new Impatiens are stabilized and are reproduced true to type in successive propagations.

The following characteristics in combination distinguish the new Impatiens Merengue from both its parent varieties and other cultivated Impatiens of this type known and used in the floriculture industry.

1. Compact growth habit.
2. Excellent self-branching.
3. Shiny, dark green foliage, infused with purple.
4. Relatively large, light pink flowers, with red-purple center eye at the base of the petals.
5. Dark green foliage and excellent branching habit make Merengue suitable for both bedding and hanging basket culture.
6. Excellent contrast between dark green foliage and pink flowers.
7. Very floriferous habit.

The accompanying color photographic drawing illustrates the overall appearance of the cultivar, with the colors being as true as it is reasonably possible to obtain in a colored reproduction of this type.

The following is a detailed description of the new Impatiens cultivar based on plants produced under commercial practice in Mishmar Hashiva, Israel. The plants described were grown in a net-covered greenhouse during the summer season with temperatures ranging from 35° C. maximum to 18° C. minimum. Color references are made to the Royal Horticultural Society Colour chart except where general terms of ordinary dictionary significance are used.

Parentage: The female parent 6 OR and the male parent 113 OR are seedlings from breeding program.

Propagation:

*Type cutting.*—Leaf cuttings.

*Time to initiate roots.*—7–8 days at 25° C. in summer; 8–9 days at 20° C. in winter.

*Rooting habit.*—Roots well.

Plant description:

*Form.*—Excellent self-branching habit produces a full, rounded symmetrical plant suitable for use as a bedding plant or in hanging basket culture.

*Habit of growth.*—Compact growth habit.

*Foliage.*—Size: Medium; mature leaves 8.0 cm long and 3.5 cm wide. Shape: Lanceolate to ovate. Margin: Serrated. Color: Young and mature foliage, top side 147A infused with purple; under side 187A; under conditions of high light intensity, slight yellow variegation on leaves will appear. Venation: Purple.

Flowering description:

*Flowering habits.*—The initiation of flower buds takes about 5–6 weeks from potting leaf cutting. Flower completely opens approximately 9–10 weeks after potting.

*Natural flowering season.*—The new cultivar flowers under ambient conditions in Israel all year, but in the winter season with less light, there are fewer flowers.

*Flower buds.*—Buds before opening are approximately 1.5 cm in length and 1.2 cm in width. Length of spur is 4.5 cm, and length of pedicel is 3.0 cm.

*Flowers borne.*—Flowers carried on strong stems are fully open from initiation in about 2 weeks; flowering continues all season.

*Quantity of flowers.*—Very floriferous; approximately 30 flowers are open at same time; flowering is continuous.

*Petals.*—Shape: Two (2) pairs of heart-shaped petals and a single larger petal; petals overlap. Color: Top side when opening 68C with 57B center eye; main color fades to 68D; under side 68C. Number of petals: Five (5). Size of flowers: Large; about 6 cm in diameter.

*Reproductive organs.*—Stamens: One (1) in number. Anthers: Round, purple color. Pollen color: White. Pistils: Stigma: Round in Shape, light green in color. Ovaries: Four (4) in number, 1 mm in size; light green in color.

Disease resistance: No significant disease problem noted to date.

I claim:

1. A new and distinct cultivar of Impatiens plant named Merengue, as illustrated and described.

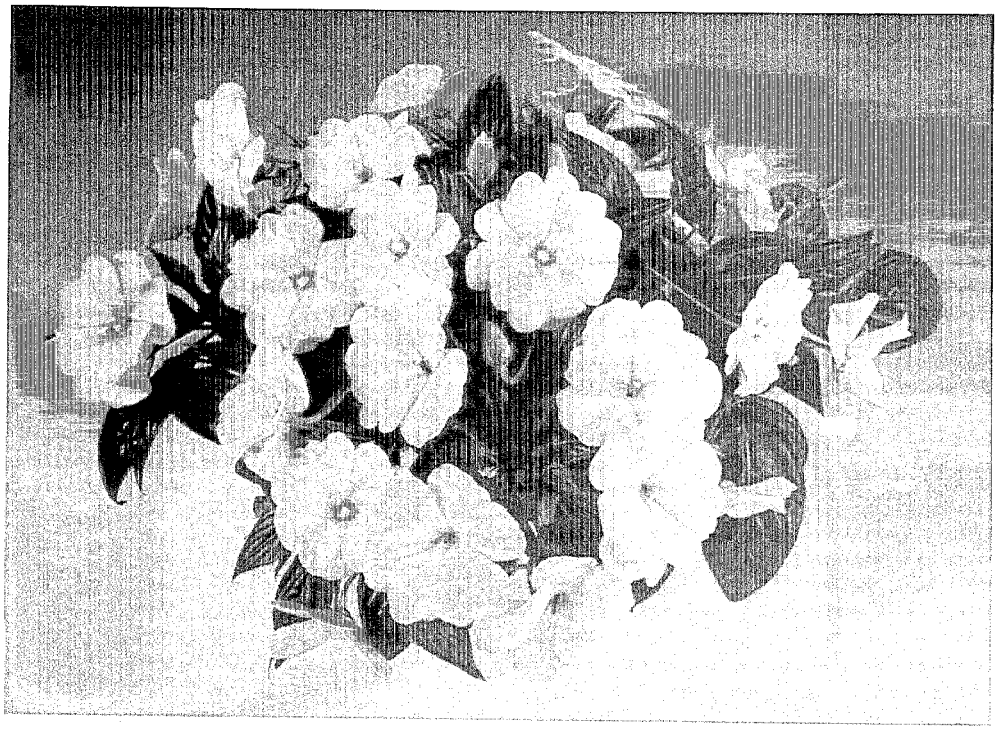

* * * * *